United States Patent
Sode (10) Patent No.: US 7,550,274 B2
(45) Date of Patent: Jun. 23, 2009

(54) GLUCOSE DEHYDROGENASE

(75) Inventor: Koji Sode, Tokyo (JP)

(73) Assignee: Ultizyme International Ltd., Tokyo (JP)

( * ) Notice: Subject to any disclaimer, the term of this patent is extended or adjusted under 35 U.S.C. 154(b) by 11 days.

(21) Appl. No.: 10/520,126

(22) PCT Filed: Jul. 2, 2003

(86) PCT No.: PCT/JP03/08418

§ 371 (c)(1),
(2), (4) Date: Oct. 4, 2005

(87) PCT Pub. No.: WO2004/005499

PCT Pub. Date: Jan. 15, 2004

(65) Prior Publication Data

US 2006/0257959 A1  Nov. 16, 2006
US 2007/0134750 A2  Jun. 14, 2007

(30) Foreign Application Priority Data

Jul. 4, 2002 (JP) ............... 2002-196177
Mar. 17, 2003 (JP) ............... 2003-071760

(51) Int. Cl.
 *C12N 9/04* (2006.01)
 *C12N 15/00* (2006.01)
 *C12Q 1/00* (2006.01)
 *C07H 21/04* (2006.01)

(52) U.S. Cl. .................. 435/26; 435/183; 435/69.1; 435/320.1; 435/190; 536/23.2

(58) Field of Classification Search .......... None
See application file for complete search history.

(56) References Cited

U.S. PATENT DOCUMENTS

2003/0232418 A1  12/2003  Takeshima et al.

FOREIGN PATENT DOCUMENTS

| EP | 1 167 519 A1 | 1/2002 |
| EP | 1 176 202 A1 | 1/2002 |
| EP | 1 367 120 A | 12/2003 |
| JP | 2001-346587 A | 12/2001 |
| WO | WO-02/34919 A1 | 5/2002 |

OTHER PUBLICATIONS

Yoshida et al., Protein Engineering, vol. 12, No. 1, pp. 63-70, (1999).
Igarashi et al., Biochemical and Biophysical Research Communication, vol. 264 pp. 820-824 (1999).
Laurinavicius et al., Talanta, vol. 52, pp. 485-493 (2000).

*Primary Examiner*—Rebecca E. Prouty
*Assistant Examiner*—Md. Younus Meah
(74) *Attorney, Agent, or Firm*—Birch, Stewart, Kolasch & Birch, LLP (57) ABSTRACT

Disclosed is a modified glucose dehydrogenase having pyrroloquinoline quinone as a coenzyme, wherein one or more amino acid residues in a region of 186-206 amino acid of water-soluble PQQGDH derived from *Acinetobacter calcoaceticus* or in an equivalent region from other species are replaced with other amino acid residues. Also disclosed is a gene coding for the modified glucose dehydrogenase of the invention, a vector comprising the gene of the invention and a transformant comprising the vector, as well as a glucose assay kit and a glucose sensor comprising the modified glucose dehydrogenase of the invention.

11 Claims, 3 Drawing Sheets

GLUCOSE DEHYDROGENASE

TECHNICAL FIELD

The present invention relates to a glucose dehydrogenase having pyrroloquinoline quinone as a coenzyme (PQQGDH), and its preparation and application to glucose quantification.

BACKGROUND OF THE INVENTION

Blood glucose concentration is a important marker for diabetes diagnosis. In addition, quantification of glucose concentration is used in monitoring the process of fermentative production using microorganisms. Conventionally, glucose quantification is performed by an enzymatic method using glucose oxidase (GOD) or glucose-6-phosphate dehydrogenase (G6PDH). However, the GOD method requires addition of catalase or peroxidase into the assay system to quantify hydrogen peroxide levels generated by oxidative reaction of glucose. G6PDH has been used for glucose quantification based on spectroscopy. This method involves the addition of coenzyme NAD(P) into the assay system.

Recently the application of PQQGDH, an enzyme which uses pyrroloquinoline quinine as a coenzyme is attracting attention, in place of the enzyme used in the existing glucose quantification method. PQQGDH is a glucose dehydrogenase having pyrroloquinoline quinone as a coenzyme, and catalyzes the reaction of oxidizing glucose to produce gluconolactone.

Two types of PQQGDHs are known: membrane-bound and water-soluble. Membrane-bound PQQGDH is a single-peptide protein with an approximate molecular weight of 87 kDa, and is found in a wide variety of gram-negative bacteria. See, for example, J. Bacteriol. (1990) 172, 6308-6315, A. M. Cleton-Jansen et al. On the other hand, water-soluble PQQGDH has been found in some strains of *Acinetobacter calcoaceticus* (Biosci. Biotech. Biochem. (1995), 59 (8), 1548-1555), and its structural gene has been cloned and its amino acid sequence determined (Mol. Gen. Genet. (1989), 217:430-436). Water-soluble PQQGDH derived from *A. calcoaceticus* is a homodimer enzyme with an approximate molecular weight of 50 kDa. It shows little homology in primary structure with other PQQ enzymes.

Recently, the results of X-ray structural analysis of water-soluble PQQGDH were published and its conformation and active center were revealed (A. Oubrie, et al. (1999) J. Mol. Bio., 289, 319-333, A. Oubrie, et al. (1999) The EMBO Journal, 18 (19), 5187-5194, and A. Oubrie, et al. (1999), PNAS 96 (21), 11787-11791). These reports demonstrate that water-soluble PQQGDH is a β-propeller protein consisting of six W-motifs.

PQQGDH is expected to have potential in glucose assays, for example, as a recognition device of a glucose sensor, because it has highly oxidative activity towards glucose and does not require oxygen as an electron acceptor as it is complexed with a coenzyme. However, the low selectivity of PQQGDH for glucose was an obstacle to this use.

The object of this invention is to provide a modified water-soluble PQQGDH with a high selectivity for glucose.

DISCLOSURE OF THE INVENTION

As a result of extensive research to engineer conventional water-soluble PQQGDH to develop a PQQGDH which shows a higher selectivity for glucose and can be applied to clinical diagnosis and food analysis, the inventor successfully obtained an enzyme with higher selectivity by introducing amino acid mutations at certain regions of water-soluble PQQGDH.

The present invention provides a modified water-soluble glucose dehydrogenase having pyrroloquinoline quinone as a coenzyme, wherein one or more amino acid residues of a wild type water-soluble glucose dehydrogenase are replaced with other amino acid residues and having high selectivity for glucose compared with the wild type water-soluble glucose dehydrogenase. The modified glucose dehydrogenase of the invention has higher glucose selectivity compared to the wild type water-soluble glucose dehydrogenase. Preferably, the modified glucose dehydrogenase of the invention has lower reactivity to lactose and maltose than to glucose compared to the wild type enzyme. More preferably, the modified glucose dehydrogenase of the invention has reactivity to lactose or maltose of less than 50%, even more preferably 40%, and most preferably 30% of the reactivity to glucose (100%).

One aspect of the invention provides a modified glucose dehydrogenase wherein one or more amino acid residues in a region of 186-206 amino acid of water-soluble PQQGDH derived from *Acinetobacter calcoaceticus* or in an equivalent region from other species are replaced with other amino acid residues (i.e., amino acid residues different from those found in a naturally occurring PQQ glucose dehydrogenase). Note that the amino acid numbering in this specification starts from the initiator methionine as the +1 position.

As used herein, the term "equivalent" with reference to the positions or regions of amino acid residues means that some amino acid residues or regions have an equivalent biological or biochemical function in two or more proteins which are structurally similar but not identical. For example, a certain region in water-soluble PQQGDH derived from organisms other than *Acinetobacter calcoaceticus* is said to be "equivalent to the region of amino acid residues 162-182 of water-soluble PQQGDH derived from *Acinetobacter calcoaceticus*" when the amino acid sequence of such a region has a high similarity to the amino acid sequence in the 162-182 region of water-soluble PQQGDH derived from *Acinetobacter calcoaceticus*, and the same function can be reasonably predicted based on the secondary structure of the relevant regions in the proteins. Additionally, the 7th amino acid residue of that region is said to be "an amino acid residue at the equivalent position to the amino acid residue 168 of water-soluble PQQGDH derived from *Acinetobacter calcoaceticus*".

Preferably, in the modified glucose dehydrogenase of the invention, glutamine at position 168 or leucine at position 169 of the amino acid sequence defined in SEQ ID NO: 1 of water-soluble PQQGDH derived from *Acinetobacter calcoaceticus* or an amino acid residue in an equivalent position from other species are replaced with another amino acid residues.

In another aspect, the invention features a modified glucose dehydrogenase having pyrroloquinoline quinone as a coenzyme wherein glutamine at position 168 of the amino acid sequence defined in SEQ ID NO: 1 is replaced with another amino acid residue. Preferably, glutamine at position 168 of the amino acid sequence defined in SEQ ID NO: 1 is replaced with alanine, glycine, glutamic acid, leucine, phenylalanine, serine or aspartic acid.

In another aspect, the invention features a modified glucose dehydrogenase having pyrroloquinoline quinone as a coenzyme wherein both glutamine at position 168 and aspartate at position 143 of the amino acid sequence defined in SEQ ID NO: 1 are replaiced with other amino acid residues. Preferably, glutamine at position 168 of the ammo acid sequence defined in SEQ ID NO: 1 is replaced with alanine, glycine, glutamic acid, leucine, phenylalanine, seine or aspartic acid. More preferably, aspartate at position 143 of the amino acid sequence defined in SEQ ID NO: 1 is replaced with glutamic acid, and glutamine at position 168 is replaced with alanine, glycine, glutamic acid, leucine, phenylalanine, seine or aspartic acid.

In another aspect, the invention features a modified glucose dehydrogenase having pyrroloquinoline quinone as a coenzyme wherein aspartate at position 143 of the amino acid sequence defined in SEQ ID NO: 1 is replaced with another amino acid residue, and asparagine at position 428 is replaced with another amino acid residue. Preferably, spartate at position 143 of the amino acid sequence defined in SEQ ID NO: 1 is replaced with glutamic acid. More preferably, aspartate at position 143 of the amino acid sequence defined in SEQ ID NO: 1 is replaced wit glutamic acid, and asparagine at position 428 is replaced with threonine.

In another aspect, the invention features a modified glucose dehydrogenase having pyrroloquinoline quinone as a coenzyme wherein glutamine at position 168 of the amino acid sequence defined in SEQ ID NO: 1 is replaced with another amino acid residue, and asparagine at position 428 is replaced with another amino acid residue. Preferably, glutamine at position 168 of the amino acid sequence defined in SEQ ID NO: 1 is replaced with alanine, glycine, glutamic acid, leucine, phenylalanine, seine or aspartic acid, and asparagine at position 428 is replaced wit another amino acid residue. More preferably, glutamine at position 168 of the amino acid sequence defined in SEQ ID NO: 1 is replaced with alanine, glycine, glutamic acid, leucine, phenylalanine, serine or aspartic acid, and asparagine at position 428 is replaced with threonine.

In another aspect, the invention features a modified glucose dehydrogenase having pyrroloquinoline quinone as a coenzyme wherein leucine at position 169 of the amino acid sequence defined in SEQ ID NO: 1 is replaced with another amino acid residue. Preferably, leucine at position 169 of the antno acid sequence defined in SEQ ID NO: 1 is replaced with alanine, glycine, methionine, tryptophan or lysine.

In another aspect, the modified glucose dehydrogenase of the invention comprises the amino acid sequence:

Gly-Arg-Asn-Xaa1-Xaa2-Ala-Tyr-Leu   (SEQ ID NO: 3)

wherein Xaa1 and Xaa2 are independently any amino acid residues, provided that when Xaa1 is Gln, then Xaa2 is not Leu. Preferably, Xaa1 is Ala, Gly, Glu, Leu, Phe, Ser or Asp, and Xaa2 is Ala or Gly.

The invention also provides a gene coding for the modified glucose dehydrogenase of the invention, a vector comprising the gene of the invention and a transformant comprising the vector, as well as a glucose assay kit and a glucose sensor comprising the modified glucose dehydrogenase of the invention.

Since the enzyme protein of the modified glucose dehydrogenase of the invention shows high selectivity and high oxidization activity to glucose, it can be applied to highly specific and sensitive measurement of glucose.

DETAILED EXPLANATIONS OF THE INVENTION

Structure of Modified PQQGDH

In a preferred modified glucose dehydrogenase of the invention, one or more amino acid residues in the 162-182 amino acid region of water-soluble PQQGDH derived from *Acinetobacter calcoaceticus* or in an equivalent region from other species are replaced with other amino acid residues. Preferably, glutamine at position 168 of the amino acid sequence defined in SEQ ID NO: 1 is replaced with alanine or glycine, and/or leucine at position 169 is replaced with alanine, glycine, methionine, tryptophan or lysine.

In another aspect of the modified PQQGDH of the invention, in addition to the modifications as described above, aspartate at position 143 of the amino acid sequence defined in SEQ ID NO: 1 is also replaced with another amino acid, preferably with glutamic acid. Also preferably, in the modified PQQGDH of the present invention, in addition to the modifications as described above, asparagine at position 428 of the amino acid sequence defined in SEQ ID NO: 1 is also replaced with another amino acid, preferably with threonine. Involvement of aspartate at position 143 and asparagine at position 428 of the amino acid sequence defined in SEQ ID NO: 1 in recognition and binding of substrate by PQQGDH is described in Japanese Patent Public Disclosure Nos. 2001-346587 and 2001-197888, respectively. In general, however, no prediction can be made regarding the changes of substrate selectivity and enzyme activity which may be caused by simultaneously altering the amino acid residues in different domains. In some cases the enzyme activity will be completely abolished. Therefore, it was a surprising discovery in the present invention that improved selectivity for glucose can be achieved by introducing double mutations.

In another aspect, the modified glucose dehydrogenase of the present invention comprises the amino acid sequence: Gly-Arg-Asn-Xaa1-Xaa2-Ala-Tyr-Leu (SEQ ID NO: 3) wherein Xaa1 and Xaa2 are independently any amino acid residues, provided that when Xaa1 is Gln, then Xaa2 is not Leu. Preferably, Xaa1 is Ala, Gly, Glu, Leu, Phe, Ser or Asn, and Xaa2 is Ala or Gly.

Preparation Method of Modified PQQGDH

The sequence of the gene encoding wild type water-soluble PQQGDH derived from *Acinetobacter calcoaceticus* is defined in SEQ ID NO:2. Genes encoding modified PQQGDHs of the present invention can be constructed by replacing the nucleotide sequences encoding certain amino acids of the wild type water-soluble PQQGDH with the nucleotide sequences encoding the amino acids to be replaced. A wide range of methods for site-specific mutagenesis have been elaborated in the art, as described in, for example, Sambrook et al., "Molecular cloning; A Laboratory Manual", second edition, 1989, Cold Spring Harbor Laboratory Press, New York.

The mutant gene obtained in this manner is inserted into an expression vector (such as a plasmid) and transformed into an appropriate host (such as *E. coli*). A wide variety of host-vector systems have been developed in the art to express exogenous proteins. For example, bacteria, yeast, and cultured cells can be used as hosts.

As long as its glucose dehydrogenase activity is retained, the modified PQQGDH of the invention can further contain deletion, substitution or addition of other amino acid residues. A wide range of methods for site-specific substitution are available in the art.

Moreover, those skilled in the art can determine a region in a water-soluble PQQGDH derived from other bacteria which is equivalent to the region of the amino acid residues 162-182 of the water-soluble PQQGDH derived from *Acinetobacter calcoaceticus* by comparing the array of the primary structure of the proteins, or by comparing the secondary structures predicted from the primary structures of the enzymes. Thus, additional modified glucose dehydrogenases with improved glucose selectivity can be obtained by substituting amino acid residues in this region with another amino acid residues. Such modified glucose dehydrogenases are also within the scope of the present invention.

After culturing the transformants expressing modified PQQGDH, obtained as described above, the cells are collected by centrifugation and then crushed by French press, or the periplasmic enzymes may be released into the medium by osmotic shock. After ultracentrifugation, water soluble fractions containing PQQGDH can be obtained. Alternatively, expressed PQQGDH can be secreted into the culture by using an appropriate host-vector system. The water soluble fraction thus obtained is then purified by ion-exchange chromatography, affinity chromatography or HPLC, to obtain the modified PQQGDH of the invention.

Measurement of Enzyme Activity

The PQQGDH of the present invention catalyzes oxidation of glucose to produce gluconolactone using PQQ as a coenzyme. The enzyme activity can be quantified by color-developing reaction of a redox dye to measure the amount of PQQ reduced with glucose oxidation by PQQGDH. Example of color-developing reagents include PMS (Phenazine methosulfate), DCIP (2,6-dichlorophenolindophenol), potassium ferricyanide, and ferrocene.

Glucose Selectivity

The glucose selectivity of the present invention can be evaluated by measuring relative enzyme activity with respect to the activity for glucose by using a variety of sugars such as 2-deoxy-D-glucose, mannose, allose, 3-o-methyl-D-glucose, galactose, xylose, lactose, and maltose as a substrate.

The modified PQQGDH of the present invention shows improved glucose selectivity compared with wild type enzyme. Especially it has high reactivity to glucose compared with that to maltose. Therefore, the assay kit and enzyme sensor prepared using the modified enzyme of the invention will exhibit high selectivity for glucose, and will have advantages in detecting glucose with high sensitivity even in samples containing variety of sugars.

Glucose Assay Kit

The present invention also provides a glucose assay kit containing the modified PQQGDH of the invention. The glucose assay kit of the invention may contain a sufficient quantity of the modified PQQGDH to carry out at least one assay. Besides modified PQQGDH, the kit may typically comprise buffers required for assay, a mediator, a standard solution of glucose to generate a calibration curve, and instructions for use. The modified PQQGDH can be supplied in a variety of forms, for example, as freeze-dried reagent or appropriate stock solutions. Preferably, the modified PQQGDH of the present invention may be supplied in the form of a holoenzyme, but can be supplied in the form of apoenzyme and converted into a holoenzyme before use.

Glucose Sensor

The present invention also provides a glucose sensor containing the modified PQQGDH of the invention. Carbon, gold, or platinum may be used as an electrode, and the enzyme of the present invention is immobilized on the electrode. Immobilization methods includes, for example, methods using cross-linking reagents, inclusion into a macromolecular matrix, coating with dialysis membrane, methods using photo-crosslinking polymer, electric conductive polymer, and redox polymer. The enzyme can also be immobilized in a polymer or adsorbed on the electrode together with an electron mediator, such as ferrocene or its derivative. Combinations of the above may also be used. Preferably, the modified PQQGDH of the present invention is immobilized on the electrode in the form of a holoenzyme, but can also be immobilized in the form of apoenzyme and PQQ is supplied as another layer or in solution. Typically, the modified PQQGDH of the present invention is immobilized on the electrode using glutaraldehyde, then free functional moieties of glutaraldehyde are blocked by treatment with a reagent having amine groups.

Measurement of glucose concentration is carried out as described below. Buffer, PQQ, $CaCl_2$, and a mediator are placed into a constant-temperature cell and are kept at a constant temperature. Potassium ferricyanide and phenazine methosulfate may be used as a mediator. An electrode in which the modified PQQGDH of the present invention is immobilized are used as a working electrode, together with a counter electrode (e.g., platinum) and a reference electrode (e.g., Ag/AgCl electrode). A constant voltage is applied to the carbon electrode. After the current reaches a constant value, a glucose-containing sample is added and the increase in the current is measured. The glucose concentration in the sample can be calculated using a calibration curve generated by standard concentration glucose solutions.

All patents and references cited in this specification are incorporated by reference. All the contents disclosed in the specifications and drawings of Japanese Patent Application Nos. 2003-71760 and 2002-196177, on which the application claims priority, are incorporated herein by reference.

The working examples described below further illustrate the invention without limiting the present invention.

EXAMPLE 1

Construction of gene encoding modified PQQGDH enzyme

Figure 1:
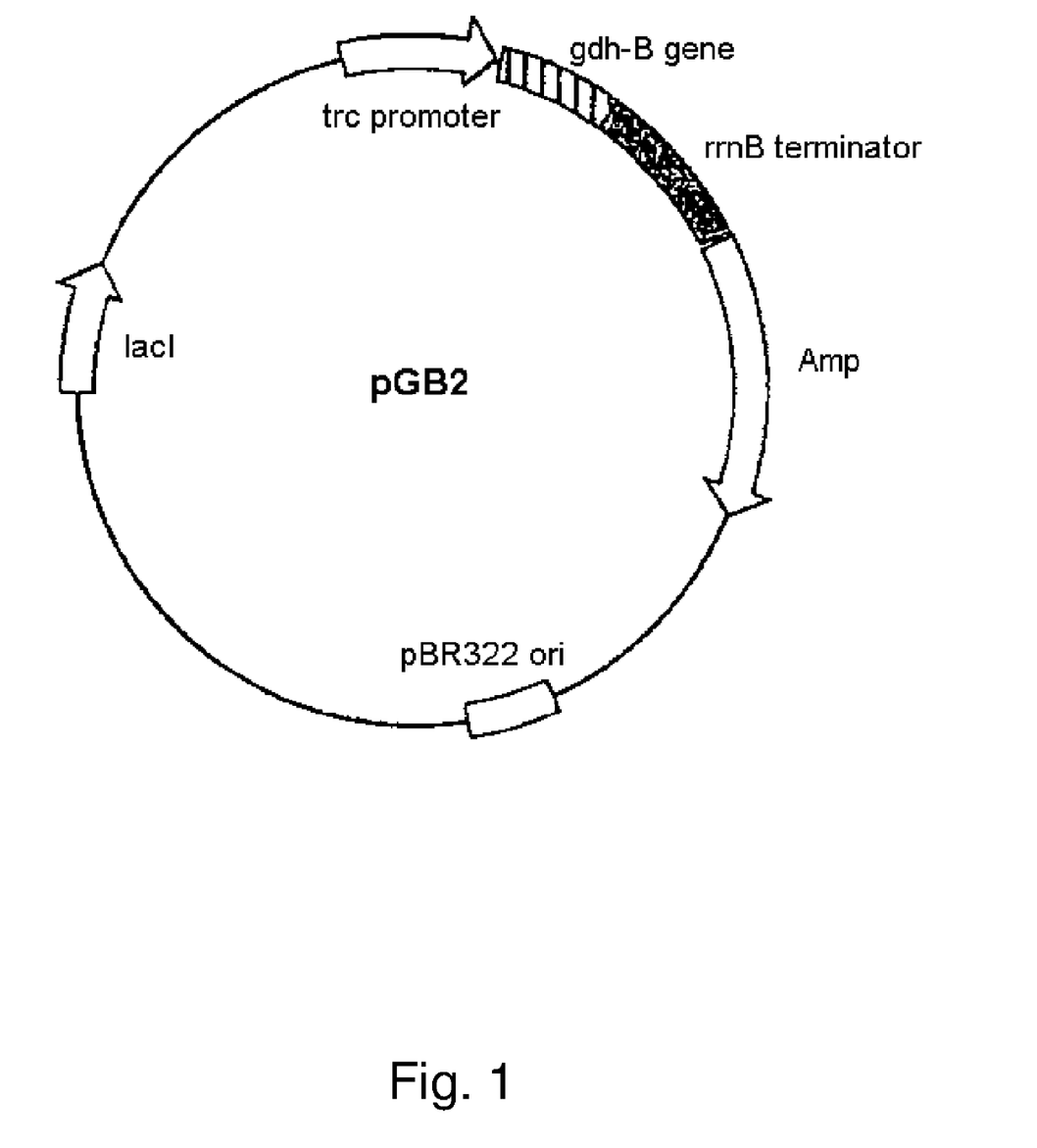
FIG. 1 shows a structure of pGB2 plasmid used to construct mutant genes encoding modified PQQGDHs of the present invention.
Figure 2:
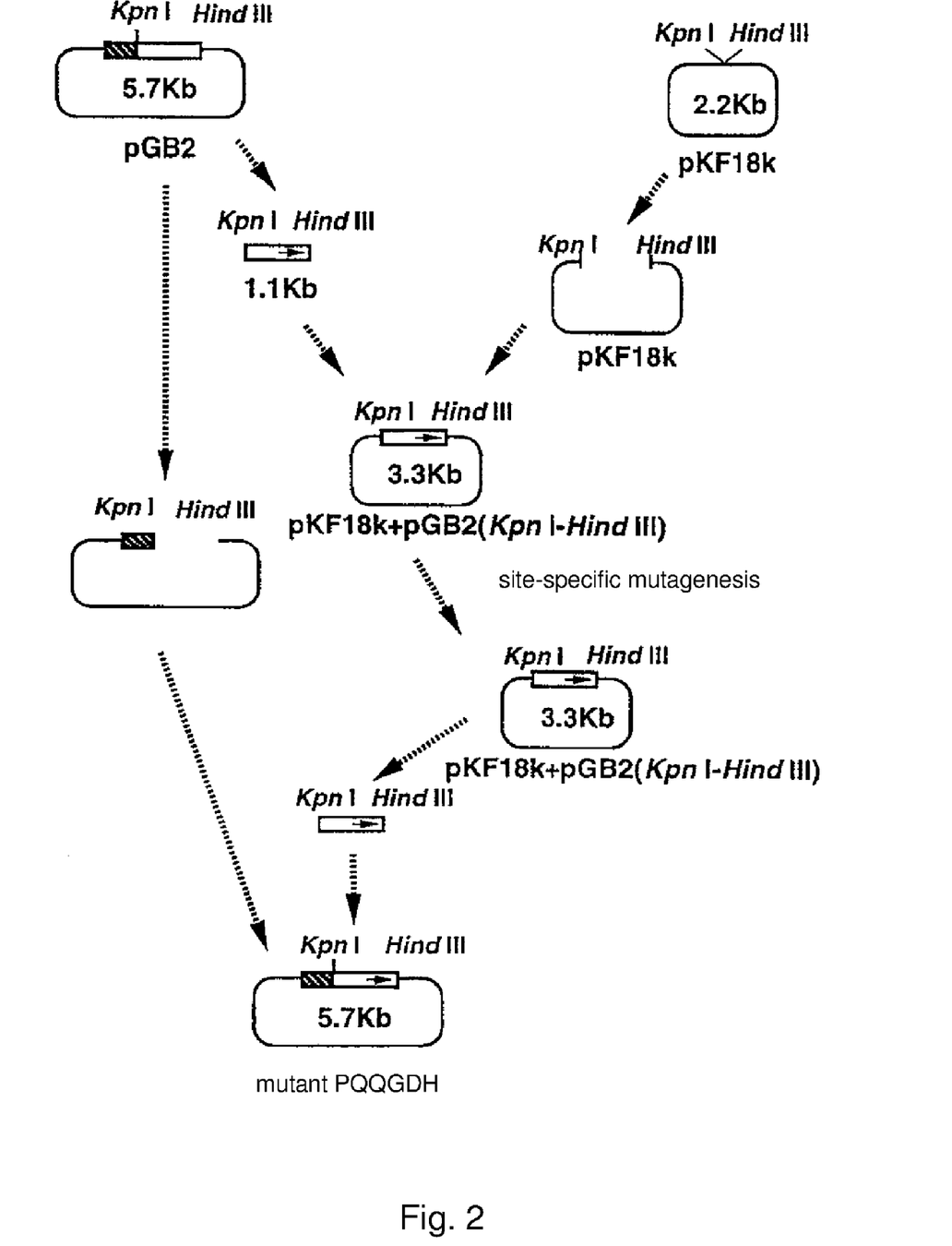
FIG. 2 shows a method of constructing mutant genes encoding modified PQQGDHs of the present invention.

Mutagenesis was carried out based on the structural gene of PQQGDH derived from *Acinetobacter calcoaceticus* (SEQ ID NO:2). pGB2 plasmid was constructed by inserting the structural gene of PQQGDH derived from *Acinetobacter calcoaceticus* into the multi-cloning site of pTrc99A vector (Pharmacia) (FIG.1). The nucleotide sequence encoding glutamine at position 168 or leucine at position 169 of the amino acid sequence defined SEQ ID NO: 1 was replaced with the nucleotide sequence encoding alanine, glycine, methionine, tryptophan or lysine by standard method of site-directed mutagenesis. Also the nucleotide sequence encoding aspartate at position 143 and asparagine at position 428 of the amino acid sequence defined in SEO ID NO: 1 was replaced with the nucleotide sequence encoding glutamic acid and glycine, respectively. Site specific mutagenesis was performed using the pGB2 plasmid as shown in F*i*g.2. The sequences of synthetic oligonucleotide target primers used for mutagenesis are shown in Table 1. In order to construct a mutant containing two mutations, two oligonucleotide target primers were used simultaneously for mutagenesis.

TABLE 1

```
Gln168Ala 5'-ata agc aag cgg gtt acg ccc-3'
Gln168Gly 5'-caa ata agc aag ccc gtt acg ccc ttg-3'
Gln168Leu 5'-caa ata agc aag cag gtt acg ccc ttg-3'
Gln168Phe 5'-caa ata agc aag aaa gtt acg ccc ttg-3'
Gln168Ser 5'-caa ata agc aag gct gtt acg ccc ttg-3'
Gln168Asn 5'-caa ata agc aag gtt gtt acg ccc ttg-3'
Gln168Asp 5'-caa ata agc aag atc gtt acg ccc ttg-3'
Gln168Glu 5'-caa ata agc aag ttc gtt acg ccc ttg-3'
Gln168Lys 5'-caa ata agc aag ttt gtt acg ccc ttg-3'
Leu169Ala 5'-caa ata agc agc ctg gtt acg-3'
Leu169Gly 5'-gaa caa ata agc acc ctg gtt acg ccc-3'
Leu169Met 5'-gaa caa ata agc cat ctg gtt acg ccc-3'
Leu169Trp 5'-gaa caa ata agc ttt ctg gtt acg ccc-3'
Leu169Lys 5'-gaa caa ata agc cca ctg gtt acg ccc-3'
Asp143Glu 5'-cc tga ctg atg ttc ttt tga tga agg-3'
Asn428Thr 5'-c atc ttt ttg gac agt tcc ggc agt
          at-3'
```

Table 1 shows SEQ ID NOS: 4, 5, 10-16, 6, 7, 17-19, 8, and 9 respectively

A template was prepared by inserting the KpnI-HindIII fragment containing part of the gene encoding PQQGDH derived from *Acinetobacter calcoaceticus* into pKF18k vector plasmid (TaKaRa). A mixture of template (50 fmol), selection primer (5 pmol) supplied in Mutan-Express Km kit, phosphorylated target primer (50 pmol), and the annealing buffer supplied in the kit (1/10 of total volume (20 μl)) was prepared, and plasmid DNA was denatured to single-strand by heating at 100° C. for 3 minutes. The selection primer was designed for the reversion of double-amber mutation on the Kanamycin resistance gene of the pKF18k plasmid. Plasmid DNA was put on ice for 5 minutes for annealing of the primers. A complementary strand was synthesized by adding the following reagents: 3 μl of extension buffer supplied in the kit, 1 μl of T4 DNA ligase, 1 μl of T4 DNA polymerase, and 5 μl of sterilized water. *E. coli* BMH71-18mutS, a DNA mismatch repair deficient strain, was transformed with the synthesized DNA and cultured overnight with vigorous shaking to amplify the plasmid.

Then, the plasmid was extracted from the bacteria and transformed into *E. coli* MV1184, and the plasmid was extracted from the colonies. The sequence of the plasmid was determined to confirm successful introduction of the desired mutations. Kpn I-Hind III gene fragment encoding wild type PQQGDH on pGB2 plasmid was replaced with the fragment containing the mutation to construct a series of mutated PQQGDH genes.

EXAMPLE 2

Preparation of Modified Enzyme

A gene encoding wild type or modified PQQGDH was inserted into the multi-cloning site of pTrc99A (Pharmacia), and the constructed plasmid was transformed into *E. coli* DH5α. Transformants were cultured in 450 ml of L-broth containing 50 μg/ml of ampicillin and 30 μg/ml of chloramphenicol using a Sakaguchi flask at 37° C. with vigorous shaking, and then inoculated in 7 L of L-broth containing 1 mM $CaCl_2$ and 500 μM PQQ. After three hours of cultivation, IPTG was added to a final concentration of 0.3 mM, and cultivation was continued for another 1.5 hours. The cells were collected by centrifugation (5000×g, 10 min, 4° C.) and washed with 0.85% NaCl twice. The cells were crushed with French press (110 MPa), and centrifuged twice (10000×g, 15 min, 4° C.) to remove the debris. The supernatant was ultracentrifuged (160,500×g (40,000 rpm), 90 min, 4° C.) to obtain a water-soluble fraction. This fraction was used in the subsequent experiments as a crude enzyme preparation.

EXAMPLE 3

Measurement of Enzyme Activity

Each of the crude enzyme preparation of wild type PQQGDH and modified PQQGDHs obtained in Example 2 was converted to a holoenzyme in the presence of 1 μM PQQ and 1 mM $CaCl_2$ for 1 hour or more. The solution was divided into aliquots of 187 μl each, and mixed with 3 μl of activation reagents (6 mM DCIPA 48 μl, 600 mM PMS 8 μl, 10 mM phosphate buffer pH 7.0 16 μl) and 10 μl of D-glucose of various concentrations to measure the enzyme activity.

Enzyme activity was measured in MOPS-NaOH buffer (pH7.0) containing PMS (phenazine methosulfate)-DCIP (2, 6-dichlorophenolindophenol). Changes in absorbance of DCIP was recorded with a spectrophotometer at 600 nm, and the reduction rate of absorbance was defined as the reaction rate of the enzyme. In this measurement, enzyme activity which reduced 1 μmol of DCIP in one minute was defined as 1 unit. The molar absorption coefficient of DCIP at pH 7.0 was 16.3 $mM^{-1}$.

Km was calculated from the plots of substrate concentration vs enzyme activity. The results are shown in Table 2.

TABLE 2

|  | Km value for glucose(mM) | Vmax (U/mg) |
| --- | --- | --- |
| Wild type | 30 | 129 |
| Gln168Ala | 50 | 123 |
| Gln168Gly | 36 | 94 |
| Leu169Ala | 177 | 42 |
| Leu169Gly | 157 | 46 |
| Leu169Met | 98 | 176 |
| Leu169Trp | 25 | 17 |
| Leu169Lys | 41 | 36 |

EXAMPLE 4

Evaluation of Substrate Specificity

Substrate specificity of the crude preparation of the modified enzymes was examined. Each of the crude enzyme preparation of wild type PQQGDH and modified PQQGDHs obtained in Example 2 was converted to a holoenzyme in the presence of 1 μM PQQ and 1 mM $CaCl_2$ for 1 hour or more. The solution was divided into aliquots of 187 μl each, and mixed with 3 μl of activation reagents (6 mM DCIPA 48 μl, 600 mM PMS 8 μl, 10 mM phosphate buffer pH 7.0 16 μl) and substrate. Solution of glucose or other sugars (400 mM) was added as a substrate to a final concentration of 20 mM or 100 mM, and the mixture was incubated for 30 minutes at room temperature. The enzyme activity was measured in the same manner as Example 3. The values were calculated as relative activity to glucose (100%). The results are shown in Table 3-6.

TABLE 3

|  | Wild type | Gln168Ala | Gln168Gly | Leu169Ala | Leu169Gly |
| --- | --- | --- | --- | --- | --- |
| Substrate conc. | 20 mM | 20 mM | 20 mM | 20 mM | 20 mM |
| Glucose | 100 (%) | 100 (%) | 100 (%) | 100 (%) | 100 (%) |
| Allose | 45 | 29 | 34 | 50 | 39 |
| 3-O-m-glucose | 82 | 80 | 101 | 66 | 60 |
| Galactose | 8 | 10 | 12 | 34 | 26 |
| Maltose | 49 | 20 | 24 | 39 | 30 |
| Lactose | 53 | 56 | 40 | 64 | 56 |
| Cellobiose | 85 | 138 | 85 | 84 | 71 |

TABLE 4

|  | Wild type | Gln168Ala | Gln168Gly | Leu169Ala | Leu169Gly |
| --- | --- | --- | --- | --- | --- |
| Substrate conc. | 100 mM | 100 mM | 100 mM | 100 mM | 100 mM |
| Glucose | 100 (%) | 100 (%) | 100 (%) | 100 (%) | 100 (%) |
| Allose | 62 | 41 | 45 | 47 | 35 |
| 3-O-m-glucose | 92 | 93 | 98 | 86 | 59 |
| Galactose | 8 | 6 | 19 | 25 | 17 |
| Maltose | 51 | 56 | 44 | 50 | 46 |
| Lactose | 51 | 56 | 44 | 50 | 46 |
| Cellobiose | 42 | 73 | 59 | 59 | 39 |

TABLE 5

|  | Wild type | | Gln168Leu | | Gln168Phe | Gln168Ser | Gln168Asp | | Gln168Glu |
| --- | --- | --- | --- | --- | --- | --- | --- | --- | --- |
| Substrate conc. | 20 mM | 100 mM | 20 mM | 100 mM | 20 mM | 20 mM | 20 mM | 100 mM | 20 mM |
| Glucose | 100 (%) | 100 (%) | 100 (%) | 100 (%) | 100 (%) | 100 (%) | 100 (%) | 100 (%) | 100 (%) |
| 2-Deoxyglucose | 0 | 5 | 0 | 0 | 0 | 2 | 0 | 0 | 0 |
| mannose | 7 | 9 | 0 | 0 | 2 | 5 | 0 | 0 | 0 |
| allose | 41 | 65 | 70 | 78 | 31 | 41 | 26 | 17 | 16 |
| 3-O-m-glucose | 80 | 97 | 84 | 90 | 62 | 89 | 46 | 50 | 63 |
| galactose | 8 | 6 | 23 | 20 | 61 | 19 | 1 | 2 | 4 |
| xylose | 5 | 8 | 17 | 26 | 28 | 7 | 0 | 0 | 0 |
| lactose | 58 | 59 | 63 | 54 | 105 | 66 | 57 | 53 | 60 |
| maltose | 67 | 55 | 55 | 36 | 31 | 35 | 8 | 1 | 8 |
| cellobiose | 85 | 44 | 90 | 55 | — | — | 148 | 82 | — |

TABLE 6

|  | Wild type | Leu169Met | Leu169Trp | Leu169Lys |
| --- | --- | --- | --- | --- |
| Substrate conc. | 20 mM | 20 mM | 20 mM | 20 mM |
| Glucose | 100 (%) | 100 (%) | 100 (%) | 100 (%) |
| Galactose | 11 | 36 | 24 | 43 |
| Xylose | 7 | 17 | 6 | 8 |
| Lactose | 61 | 59 | 76 | 48 |
| Maltose | 61 | 39 | 17 | 31 |

In addition, the enzyme activity of the modified enzyme of the present invention carrying a double mutation was measured. The results are shown in Table 7, 8. Each modified enzyme of the present invention showed higher reactivity to glucose than to maltose.

TABLE 7

|  | Asp143Glu/Asn428Thr | Gln168Gly/Asn428Thr |
| --- | --- | --- |
| Substrate conc. | 20 mM | 20 mM |
| Glucose | 100 (%) | 100 (%) |
| Allose | 2 | 32 |
| 3-O-m-glucose | 4 | 98 |
| Galactose | 2 | 14 |
| Maltose | 2 | 46 |
| Lactose | 12 | 21 |

TABLE 8

| Substrate conc. | Wild type | | Asp143Glu/<br>Leu168Ala | | Asp143Glu/<br>Leu168Gly | | Asp143Glu/<br>Gln168Leu |
|---|---|---|---|---|---|---|---|
| | 20 mM | 100 mM | 20 mM | 100 mM | 20 mM | 100 mM | 100 mM |
| Glucose | 100 (%) | 100 (%) | 100 (%) | 100 (%) | 100 (%) | 100 (%) | 100 (%) |
| 2-deoxyglucose | 0 | 5 | 0 | 0 | 0 | 0 | 0 |
| Mannose | 7 | 9 | 1 | 0 | 0 | 0 | 0 |
| Allose | 41 | 65 | 6 | 5 | 6 | 7 | 2 |
| 3-O-m-glucose | 80 | 97 | 2 | 4 | 6 | 8 | 2 |
| Galactose | 8 | 6 | 5 | 7 | 1 | 4 | 21 |
| Xylose | 5 | 8 | 0 | 1 | 0 | 0 | 5 |
| Lactose | 58 | 59 | 58 | 61 | 50 | 43 | 57 |
| Maltose | 67 | 55 | 11 | 11 | 1 | 5 | 22 |
| Cellobiose | 85 | 44 | — | 107 | 215 | 130 | 195 |

| Substrate conc. | Asp143Glu/<br>Gln168Ser | | Asp143Glu/<br>Gln168Asn | | Asp143Glu/<br>Gln168Glu | | Asp143Glu/<br>Gln168Lys |
|---|---|---|---|---|---|---|---|
| | 20 mM | 100 mM | 20 mM | 100 mM | 20 mM | 100 mM | 100 mM |
| Glucose | 100 (%) | 100 (%) | 100 (%) | 100 (%) | 100 (%) | 100 (%) | 100 (%) |
| 2-deoxyglucose | 0 | 0 | 2 | 5 | 1 | 8 | |
| Mannose | 0 | 0 | 2 | 9 | 3 | 11 | |
| Allose | 1 | 0 | 16 | 26 | 5 | 63 | |
| 3-O-m-glucose | 0 | 0 | 9 | 14 | 6 | 35 | |
| Galactose | 3 | 0 | 10 | 12 | 9 | 70 | |
| Xylose | 0 | 0 | 3 | 9 | 2 | 9 | |
| Lactose | 61 | 43 | 49 | 44 | 54 | 90 | |
| Maltose | 6 | 3 | 42 | 40 | 16 | 49 | |
| Cellobiose | 240 | 131 | — | 61 | — | 74 | |

EXAMPLE 5

Dependency on Substrate Concentration

Figure 3:
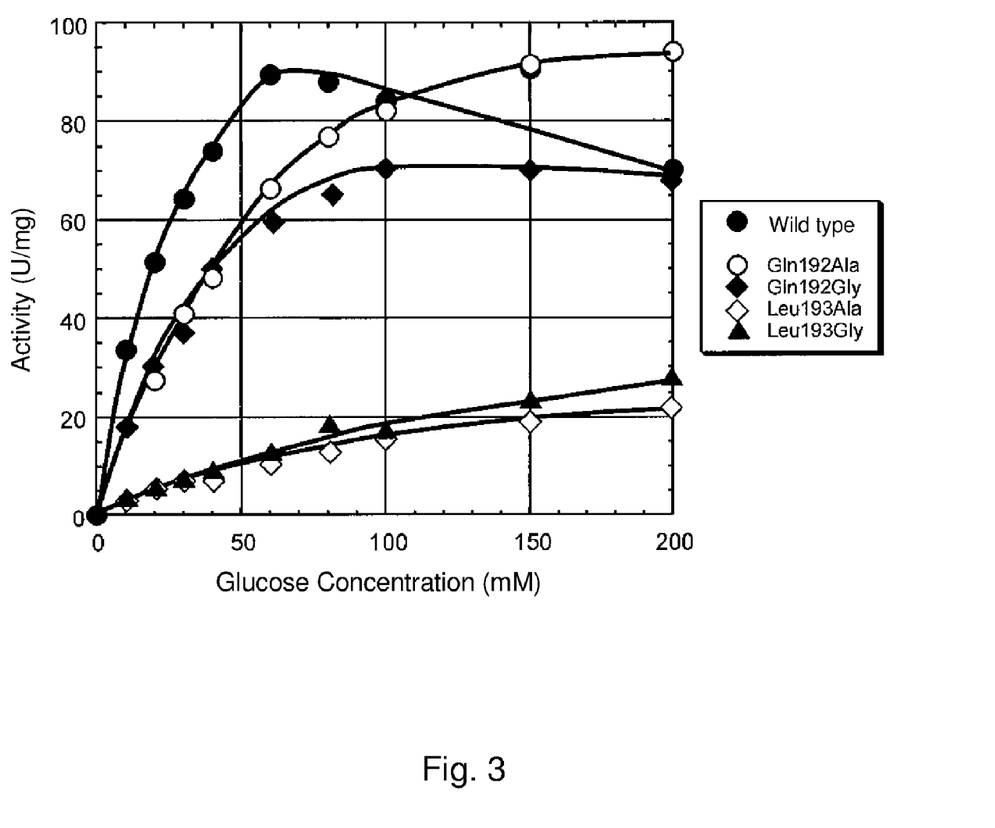
FIG. 3 is a graph showing substrate concentration dependency of the activity of the modified PQQGDHs of the present invention.

Dependency on substrate concentration of modified enzymes of the present invention was examined. Each modified enzyme was converted to a holoenzyme in the presence of 1 μM PQQ and 1 mM $CaCl_2$ for 1 hour or more. Following the method for measuring the enzyme activity described in Example 3, the changes in absorbance of DCIP were measured with a spectrophotometer at 600 nm as an indicator. The results are shown in FIG. 3. The modified PQQGDH of the present invention was saturated at higher concentration of glucose compared with the wild type. For both modified and wild type PQQGDHs, substrate inhibition was not observed up to the glucose concentration of 200 mM, and Ksi was observed to be 200 mM or more.

EXAMPLE 6

Purification of Enzyme

Each of the crude enzyme preparation of wild type and Gln192Asp obtained in Example 2 was adsorbed in a cation exchange chromatography column filled with TSKgel CM-TOYOPEARL 650M (Toso Co.) and equilibrated with 10 mM phosphate buffer, pH 7.0. The column was washed with 750 ml of 10 mM phosphate buffer, pH 7.0 and the enzyme was eluted with 10 mM phosphate buffer, pH 7.0 containing from 0 M to 0.2 M NaCl. The flow rate was 5 mL/min. Fractions showing GDH activity were collected and dialyzed against 10 mM MOPS-NaOH buffer (pH 7.0) overnight. In this manner, modified PQQGDH protein was purified which exhibited a single band under electrophoresis. Enzyme activity for various substrates of the purified enzyme was measured. The results are shown in Tables 9-10.

TABLE 9

| | wild type | | | | Glu168Asp | | | |
|---|---|---|---|---|---|---|---|---|
| | Km (mM) | Vmax (U/mg) | kcat ($sec^{-1}$) | kcat/Km ($mM^{-1} \cdot sec^{-1}$) | Km (mM) | Vmax (U/mg) | kcat ($sec^{-1}$) | kcat/Km ($mM^{-1} \cdot sec^{-1}$) |
| glucose | 25.0 | 4610 | 3860 | 154 (100%) | 50.0 | 475 | 398 | 8.0 (100%) |
| allose | 35.5 | 2997 | 2509 | 71 (46%) | 57.2 | 226 | 189 | 3.3 (42%) |
| 3-O-m-glucose | 28.7 | 3596 | 3011 | 105 (68%) | 64.4 | 310 | 260 | 4.0 (51%) |
| galactose | 5.3 | 277 | 232 | 44 (29%) | 118.9 | 137 | 115 | 1.0 (12%) |
| lactose | 18.9 | 1982 | 1659 | 88 (57%) | 75.0 | 390 | 327 | 4.4 (54%) |
| maltose | 26.0 | 2305 | 1930 | 74 (48%) | 95.8 | 77 | 64 | 0.7 (8%) |

TABLE 10

| | Asp143Glu/Asn428Thr | | |
|---|---|---|---|
| | Km (mM) | kcat (sec$^{-1}$) | kcat/Km (mM$^{-1}$·sec$^{-1}$) |
| Glucose | 48 | 1193 | 25 (100%) |
| Allose | 182 | 73 | 0.4 (2%) |
| 3-O-m-glucose | 198 | 215 | 1.1 (4%) |
| Galactose | 145 | 89 | 0.6 (2%) |
| Lactose | 55 | 167 | 3 (12%) |
| Maltose | 147 | 65 | 0.4 (2%) |
| Cellobiose | 16 | 226 | 14 (56%) |

EXAMPLE 7

Preparation of Enzyme Sensor and its Evaluation

Twenty mg of carbon paste was added to 5 units of the modified enzyme Gln168Ala and freeze-dried. The mixture was applied on the surface of a carbon paste electrode filled with approximately 40 mg of carbon paste, and the electrode was polished on a filter paper. This electrode was treated with MOPS buffer (pH 7.0) containing 1% glutaraldehyde for 30 minutes at room temperature and then treated with MOPS buffer (pH 7.0) containing 20 mM lysine for 20 minutes at room temperature to block unreacted glutaraldehyde. The electrode was equilibrated in 10 mM MOPS buffer (pH 7.0) for one hour or more at room temperature, then stored at 4° C.

The glucose concentration was measured using the glucose sensor thus prepared. Glucose concentration was quantified in the range from 0.1 mM to 5 mM by using the glucose sensor prepared with the modified PQQGDH of the invention.

INDUSTRIAL APPLICABILITY

The modified water-soluble PQQGDH of the present invention has high glucose selectivity, thus is useful as a device of a sensor for measuring blood glucose level.

The invention claimed is:

1. An isolated mutant water-soluble glucose dehydrogenase having pyrroloquinoline quinone as a coenzyme, wherein said mutant is a mutant of a glucose dehydrogenase comprising the amino acid sequence of SEQ ID NO: 1, and wherein said mutant consists of an amino acid substitution selected from the group consisting of:
   (1) glutamine at position 168 of SEQ ID NO:1 is substituted with glycine, glutamic acid, leucine, phenylalanine, serine or aspartic acid, optionally combined with (a) a substitution wherein aspartate at position 143 of SEQ ID NO: 1 is substituted with glutamic acid or (b) a substitution wherein asparagine at position 428 of SEQ ID NO:1 is substituted with threonine;
   (2) leucine at position 169 of SEQ ID NO:1 substituted with alanine, glycine, methionine, tryptophan or lysine, optionally combined with (a) a substitution wherein aspartate at position 143 of SEQ ID NO:1 is substituted with glutamic acid or (b) a substitution wherein asparagine at position 428 of SEQ ID NO:1 is substituted with threonine ; and
   (3) aspartate at position 143 of SEQ ID NO:1 is substituted with glutamic acid and asparagine at position 428 of SEQ ID NO: 1 is substituted with threonine.

2. A glucose assay kit comprising the modified glucose dehydrogenase as claimed in claim 1.

3. A glucose sensor comprising the modified glucose dehydrogenase as claimed in claim 1.

4. The mutant glucose dehydrogenase as claimed in claim 1, wherein glutamine at position 168 of SEQ ID NO:1 is substituted with glycine, glutamic acid, leucine, phenylalanine, serine or aspartic acid.

5. The mutant glucose dehydrogenase as claimed in claim 1, wherein leucine at position 169 of SEQ ID NO:1 is substituted wit alanine, glycine, methionine, tryptophan or lysine.

6. The mutant glucose dehydrogenase as claimed in claim 1, wherein aspartate at position 143 of SEQ ID NO:1 is substituted with glutamic acid, and asparagine at position 428 of SEQ ID NO:1 is substituted with threonine.

7. The mutant glucose dehydrogenase as claimed in claim 1, wherein glutamine at position 168 of SEQ ID NO:1 is substituted with glycine, glutamic acid, leucine, phenylalanine, serine or aspartic acid in SEQ ID NO:1, and aspartate at position 143 of SEQ ID NO:1 is substituted wit glutamic acid.

8. The mutant glucose dehydrogenase as claimed in claim 1, wherein glutamine at position 168 of SEQ ID NO:1 is substituted with glycine, glutamic acid, leucine, phenylalanine, serine or aspartic acid in SEQ ID NO:1, and asparagine at 428 of SEQ ID NO:1 is substituted with threonine.

9. The mutant glucose dehydrogenase as claimed in claim 1, wherein leucine at position 169 of SEQ ID NO:1 is substituted with alanine, glycine, methionine, tryptophan or lysine and aspartate at position 143 of SEQ ID NO:1 is substituted wit glutamic acid.

10. The mutant glucose dehydrogenase as claimed in claim 1, wherein leucine at 169 of SEQ ID NO:1 is substituted with alanine, glycine, methionine, tryptophan or lysine and asparagine at position 428 of SEQ ID NO:1 is substituted with threonine.

11. An isolated mutant water-soluble glucose dehydrogenase having pyrroloquinoline quinone as a coenzyme, wherein said mutant is a mutant of a glucose dehydrogenase comprising the amino acid sequence of SEQ ID NO:1, and wherein said mutant consist of an amino acid substitution wherein glutamine at position 168 of SEQ ID NO:1 is substituted with glycine, glutamic acid, leucine, phenylalanine, serine or aspartic acid.

* * * * *

SEQUENCE LISTING

<160> NUMBER OF SEQ ID NOS: 19

<210> SEQ ID NO 1
<211> LENGTH: 454
<212> TYPE: PRT
<213> ORGANISM: Acinetobacter calcoaceticus

<400> SEQUENCE: 1

Asp Val Pro Leu Thr Pro Ser Gln Phe Ala Lys Ala Lys Ser Glu Asn
 1               5                  10                  15

Phe Asp Lys Lys Val Ile Leu Ser Asn Leu Asn Lys Pro His Ala Leu
            20                  25                  30

Leu Trp Gly Pro Asp Asn Gln Ile Trp Leu Thr Glu Arg Ala Thr Gly
        35                  40                  45

Lys Ile Leu Arg Val Asn Pro Glu Ser Gly Ser Val Lys Thr Val Phe
    50                  55                  60

Gln Val Pro Glu Ile Val Asn Asp Ala Asp Gly Gln Asn Gly Leu Leu
65                  70                  75                  80

Gly Phe Ala Phe His Pro Asp Phe Lys Asn Asn Pro Tyr Ile Tyr Ile
                85                  90                  95

Ser Gly Thr Phe Lys Asn Pro Lys Ser Thr Asp Lys Glu Leu Pro Asn
            100                 105                 110

Gln Thr Ile Ile Arg Arg Tyr Thr Tyr Asn Lys Ser Thr Asp Thr Leu
        115                 120                 125

Glu Lys Pro Val Asp Leu Leu Ala Gly Leu Pro Ser Ser Lys Asp His
    130                 135                 140

Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Pro Asn
                165                 170                 175

Gln Ala Gln His Thr Pro Thr Gln Gln Glu Leu Asn Gly Lys Asp Tyr
            180                 185                 190

His Thr Tyr Met Gly Lys Val Leu Arg Leu Asn Leu Asp Gly Ser Ile
        195                 200                 205

Pro Lys Asp Asn Pro Ser Phe Asn Gly Val Val Ser His Ile Tyr Thr
    210                 215                 220

```
Leu Gly His Arg Asn Pro Gln Gly Leu Ala Phe Thr Pro Asn Gly Lys
225                 230                 235                 240

Leu Leu Gln Ser Glu Gln Gly Pro Asn Ser Asp Asp Glu Ile Asn Leu
            245                 250                 255

Ile Val Lys Gly Gly Asn Tyr Gly Trp Pro Asn Val Ala Gly Tyr Lys
        260                 265                 270

Asp Asp Ser Gly Tyr Ala Tyr Ala Asn Tyr Ser Ala Ala Ala Asn Lys
    275                 280                 285

Ser Ile Lys Asp Leu Ala Gln Asn Gly Val Lys Val Ala Ala Gly Val
290                 295                 300

Pro Val Thr Lys Glu Ser Glu Trp Thr Gly Lys Asn Phe Val Pro Pro
305                 310                 315                 320

Leu Lys Thr Leu Tyr Thr Val Gln Asp Thr Tyr Asn Tyr Asn Asp Pro
            325                 330                 335

Thr Cys Gly Glu Met Thr Tyr Ile Cys Trp Pro Thr Val Ala Pro Ser
        340                 345                 350

Ser Ala Tyr Val Tyr Lys Gly Gly Lys Lys Ala Ile Thr Gly Trp Glu
    355                 360                 365

Asn Thr Leu Leu Val Pro Ser Leu Lys Arg Gly Val Ile Phe Arg Ile
370                 375                 380

Lys Leu Asp Pro Thr Tyr Ser Thr Thr Tyr Asp Asp Ala Val Pro Met
385                 390                 395                 400

Phe Lys Ser Asn Asn Arg Tyr Arg Asp Val Ile Ala Ser Pro Asp Gly
            405                 410                 415

Asn Val Leu Tyr Val Leu Thr Asp Thr Ala Gly Asn Val Gln Lys Asp
        420                 425                 430

Asp Gly Ser Val Thr Asn Thr Leu Glu Asn Pro Gly Ser Leu Ile Lys
    435                 440                 445

Phe Thr Tyr Lys Ala Lys
    450

<210> SEQ ID NO 2
<211> LENGTH: 1612
<212> TYPE: DNA
<213> ORGANISM: Acinetobacter calcoaceticus

<400> SEQUENCE: 2
agctactttt atgcaacaga gcctttcaga aatttagatt ttaatagatt cgttattcat      60
cataatacaa atcatataga gaactcgtac aaacccttta ttagaggttt aaaaattctc     120
ggaaaatttt gacaatttat aaggtggaca catgaataaa catttattgg ctaaaattgc     180
tttattaagc gctgttcagc tagttacact ctcagcattt gctgatgttc ctctaactcc     240
atctcaattt gctaaagcga atcagagaa ctttgacaag aaagttattc tatctaatct     300
aaataagccg catgctttgt tatggggacc agataatcaa atttggttaa ctgagcgagc     360
aacaggtaag attctaagag ttaatccaga gtcgggtagt gtaaaaacag tttttcaggt     420
accagagatt gtcaatgatg ctgatgggca gaatggttta ttaggttttg ccttccatcc     480
tgattttaaa aataatcctt atatctatat ttcaggtaca tttaaaaatc gaaatctac     540 agataaagaa ttaccgaacc aaacgattat tcgtcgttat acctataata atcaacaga     600 tacgctcgag aagccagtcg atttattagc aggattacct tcatcaaaag accatcagtc     660
aggtcgtctt gtcattgggc cagatcaaaa gattttattat acgattggtg accaagggcg     720
taaccagctt gctatttgt tcttgccaaa tcaagcacaa catacgccaa ctcaacaaga     780
```

```
actgaatggt aaagactatc acacctatat gggtaaagta ctacgcttaa atcttgatgg    840
aagtattcca aaggataatc caagttttaa cggggtggtt agccatattt atacacttgg    900
acatcgtaat ccgcagggct tagcattcac tccaaatggt aaattattgc agtctgaaca    960
aggcccaaac tctgacgatg aaattaacct cattgtcaaa ggtggcaatt atggttggcc   1020
gaatgtagca ggttataaag atgatagtgg ctatgcttat gcaaattatt cagcagcagc   1080
caataagtca attaaggatt tagctcaaaa tggagtaaaa gtagccgcag gggtccctgt   1140
gacgaaagaa tctgaatgga ctggtaaaaa ctttgtccca ccattaaaaa ctttatatac   1200
cgttcaagat acctacaact ataacgatcc aacttgtgga gagatgacct acatttgctg   1260
gccaacagtt gcaccgtcat ctgcctatgt ctataagggc ggtaaaaaag caattactgg   1320
ttgggaaaat acattattgg ttccatcttt aaaacgtggt gtcattttcc gtattaagtt   1380
agatccaact tatagcacta cttatgatga cgctgtaccg atgtttaaga gcaacaaccg   1440
ttatcgtgat gtgattgcaa gtccagatgg gaatgtctta tatgtattaa ctgatactgc   1500
cggaaatgtc caaaaagatg atggctcagt aacaaataca ttagaaaacc caggatctct   1560
cattaagttc acctataagg ctaagtaata cagtcgcatt aaaaaaccga tc           1612
```

<210> SEQ ID NO 3
<211> LENGTH: 8
<212> TYPE: PRT
<213> ORGANISM: Acinetobacter calcoaceticus
<220> FEATURE:
<221> NAME/KEY: misc_feature
<222> LOCATION: (4)..(5)
<223> OTHER INFORMATION: Xaa can be any amino acid provided that when
      Xaa at pos. 4 is Gln, then Xaa at pos. 5 is not Leu

<400> SEQUENCE: 3

Gly Arg Asn Xaa Xaa Ala Tyr Leu
1               5

<210> SEQ ID NO 4
<211> LENGTH: 21
<212> TYPE: DNA
<213> ORGANISM: Artificial Sequence
<220> FEATURE:
<223> OTHER INFORMATION: synthetic primer for point mutation

<400> SEQUENCE: 4
ataagcaagc gggttacgcc c                                                21

<210> SEQ ID NO 5
<211> LENGTH: 27
<212> TYPE: DNA
<213> ORGANISM: Artificial Sequence
<220> FEATURE:
<223> OTHER INFORMATION: synthetic primer for point mutation

<400> SEQUENCE: 5
caaataagca agcccgttac gcccttg                                          27

<210> SEQ ID NO 6
<211> LENGTH: 21
<212> TYPE: DNA
<213> ORGANISM: Artificial Sequence
<220> FEATURE:
<223> OTHER INFORMATION: synthetic primer for point mutation

<400> SEQUENCE: 6
caaataagca gcctggttac g    21

<210> SEQ ID NO 7
<211> LENGTH: 27
<212> TYPE: DNA
<213> ORGANISM: Artificial Sequence
<220> FEATURE:
<223> OTHER INFORMATION: synthetic primer for point mutation

<400> SEQUENCE: 7
gaacaaataa gcaccctggt tacgccc    27

<210> SEQ ID NO 8
<211> LENGTH: 26
<212> TYPE: DNA
<213> ORGANISM: Artificial Sequence
<220> FEATURE:
<223> OTHER INFORMATION: synthetic primer for point mutation

<400> SEQUENCE: 8
cctgactgat gttcttttga tgaagg    26

<210> SEQ ID NO 9
<211> LENGTH: 27
<212> TYPE: DNA
<213> ORGANISM: Artificial Sequence
<220> FEATURE:
<223> OTHER INFORMATION: synthetic primer for point mutation

<400> SEQUENCE: 9
catcttttTg gacagttccg gcagtat    27

<210> SEQ ID NO 10
<211> LENGTH: 27
<212> TYPE: DNA
<213> ORGANISM: Artificial Sequence
<220> FEATURE:
<223> OTHER INFORMATION: synthetic primer for point mutation

<400> SEQUENCE: 10
caaataagca agcaggttac gcccttg    27

<210> SEQ ID NO 11
<211> LENGTH: 27
<212> TYPE: DNA
<213> ORGANISM: Artificial Sequence
<220> FEATURE:
<223> OTHER INFORMATION: synthetic primer for point mutation

<400> SEQUENCE: 11
caaataagca agaaagttac gcccttg    27

<210> SEQ ID NO 12
<211> LENGTH: 27
<212> TYPE: DNA
<213> ORGANISM: Artificial Sequence
<220> FEATURE:
<223> OTHER INFORMATION: synthetic primer for point mutation

<400> SEQUENCE: 12
caaataagca aggctgttac gcccttg    27

<210> SEQ ID NO 13
<211> LENGTH: 27
<212> TYPE: DNA
<213> ORGANISM: Artificial Sequence

```
<220> FEATURE:
<223> OTHER INFORMATION: synthetic primer for point mutation

<400> SEQUENCE: 13
caaataagca aggttgttac gcccttg                                              27

<210> SEQ ID NO 14
<211> LENGTH: 27
<212> TYPE: DNA
<213> ORGANISM: Artificial Sequence
<220> FEATURE:
<223> OTHER INFORMATION: synthetic primer for point mutation

<400> SEQUENCE: 14
caaataagca agatcgttac gcccttg                                              27

<210> SEQ ID NO 15
<211> LENGTH: 27
<212> TYPE: DNA
<213> ORGANISM: Artificial Sequence
<220> FEATURE:
<223> OTHER INFORMATION: synthetic primer for point mutation

<400> SEQUENCE: 15
caaataagca agttcgttac gcccttg                                              27

<210> SEQ ID NO 16
<211> LENGTH: 27
<212> TYPE: DNA
<213> ORGANISM: Artificial Sequence
<220> FEATURE:
<223> OTHER INFORMATION: synthetic primer for point mutation

<400> SEQUENCE: 16
caaataagca agtttgttac gcccttg                                              27

<210> SEQ ID NO 17
<211> LENGTH: 27
<212> TYPE: DNA
<213> ORGANISM: Artificial Sequence
<220> FEATURE:
<223> OTHER INFORMATION: synthetic primer for point mutation

<400> SEQUENCE: 17
gaacaaataa gccatctggt tacgccc                                              27

<210> SEQ ID NO 18
<211> LENGTH: 27
<212> TYPE: DNA
<213> ORGANISM: Artificial Sequence
<220> FEATURE:
<223> OTHER INFORMATION: synthetic primer for point mutation

<400> SEQUENCE: 18
gaacaaataa gctttctggt tacgccc                                              27

<210> SEQ ID NO 19
<211> LENGTH: 27
<212> TYPE: DNA
<213> ORGANISM: Artificial Sequence
<220> FEATURE:
<223> OTHER INFORMATION: synthetic primer for point mutation

<400> SEQUENCE: 19
gaacaaataa gcccactggt tacgccc                                              27
```